(12) United States Patent
Elfersy et al.

(10) Patent No.: US 8,999,357 B2
(45) Date of Patent: *Apr. 7, 2015

(54) METHODS AND COMPOSITIONS FOR BIOCIDAL TREATMENTS

(75) Inventors: Jacques Elfersy, Atlanta, GA (US); Marcello D. Villahoz, Atlanta, GA (US)

(73) Assignee: Sishield Technologies, Inc., Atlanta, GA (US)

( * ) Notice: Subject to any disclaimer, the term of this patent is extended or adjusted under 35 U.S.C. 154(b) by 645 days.

This patent is subject to a terminal disclaimer.

(21) Appl. No.: 11/349,028

(22) Filed: Feb. 7, 2006

(65) Prior Publication Data

US 2006/0193816 A1 Aug. 31, 2006

Related U.S. Application Data

(60) Provisional application No. 60/650,502, filed on Feb. 7, 2005.

(51) Int. Cl.
| | | |
|---|---|---|
| *A01N 33/12* | (2006.01) | |
| *A01N 55/10* | (2006.01) | |
| *A01N 25/08* | (2006.01) | |
| *A01N 55/00* | (2006.01) | |
| *A01N 59/00* | (2006.01) | |
| *A61K 8/41* | (2006.01) | |
| *A61K 8/898* | (2006.01) | |
| *A61Q 17/00* | (2006.01) | |
| *D06M 11/50* | (2006.01) | |
| *D06M 13/342* | (2006.01) | |
| *D06M 13/463* | (2006.01) | |
| *D06M 13/513* | (2006.01) | |
| *D06M 16/00* | (2006.01) | |

(52) U.S. Cl.
CPC ............... *A01N 55/00* (2013.01); *A01N 33/12* (2013.01); *A01N 59/00* (2013.01); *A61K 8/416* (2013.01); *A61K 8/898* (2013.01); *A61Q 17/005* (2013.01); *D06M 11/50* (2013.01); *D06M 13/342* (2013.01); *D06M 13/463* (2013.01); *D06M 13/513* (2013.01); *D06M 16/00* (2013.01)

(58) Field of Classification Search
USPC .................. 424/405, 616; 514/63, 642, 643
See application file for complete search history.

(56) References Cited

U.S. PATENT DOCUMENTS

| | | | | |
|---|---|---|---|---|
| 3,122,447 A | * | 2/1964 | Sexsmith .................. | 442/118 |
| 3,247,058 A | * | 4/1966 | Hyman ..................... | 424/404 |
| 3,997,519 A | * | 12/1976 | Armbruster ............... | 534/589 |
| 4,567,039 A | | 1/1986 | Stadnick et al. | |
| 4,908,355 A | | 3/1990 | Gettings et al. | |
| 5,145,596 A | * | 9/1992 | Blank et al. .............. | 510/513 |
| 5,180,831 A | * | 1/1993 | Powers et al. ............. | 546/291 |
| 5,206,371 A | * | 4/1993 | Powers et al. ............. | 546/290 |
| 5,411,585 A | * | 5/1995 | Avery et al. .............. | 106/287.1 |
| 5,954,869 A | | 9/1999 | Elfersy et al. | |
| 5,959,014 A | | 9/1999 | Liebeskind et al. | |
| 6,113,815 A | | 9/2000 | Elfersy et al. | |
| 6,120,587 A | | 9/2000 | Elfersy et al. | |
| 6,221,944 B1 | | 4/2001 | Liebeskind et al. | |
| 6,469,120 B1 | | 10/2002 | Elfersy et al. | |
| 6,528,472 B2 | * | 3/2003 | Charaf et al. ............. | 510/391 |
| 6,607,717 B1 | | 8/2003 | Johnson et al. | |
| 6,762,172 B1 | | 7/2004 | Elfersy et al. | |
| 7,304,022 B2 | * | 12/2007 | Cheung et al. ............ | 510/191 |
| 2003/0100465 A1 | | 5/2003 | Kilkenny et al. | |
| 2005/0008613 A1 | * | 1/2005 | Peterson et al. .......... | 424/78.27 |

OTHER PUBLICATIONS

A.J. Isquith, E.A. Abbott, and P.A. Walters, "Surface-Bonded Antimicrobial Activity of an Organosilicon Quaternary Ammonium Chloride", Applied Microbiology, 1972, 24(6), 859-863.*
P.A. Walters, E.A. Abbott, and A.J. Isquith, "Algicidal Activity of a Surface-Bonded Organosilicon Quaternary Ammonium Chloride", Applied Microbiology, 1973, 25(2), 253-256.*
Joerg C. Tiller, Chun-Jen Liao, Kim Lewis, and Alexander M. Klibanov, "Designing surfaces that kill bacteria on contact", Proceedings of the National Academy of Sciences, 2001, 98(11), 5981-5985.*
Tetsuji Kametani, Kazuo Kigasawa, Tetsutaro Hayasaka, Mineharu Hiiragi, Haruhide Ishimaru and Setsu Asagi, "Novel methylation. III. Methylation of tertiary amines such as pyridine and isoquinoline with alkyl carboxylates", Journal of Heterocyclic Chemistry, 1966, 3(2), Abstract only.*
John L. Speier and James R. Malek, "Destruction of Microorganisms by Contact with Solid Surfaces", Journal of Colloid and Interface Science, 1982, 89(1), 68-76.*
Department of Justice, United States Attorney David E. Nahmias, Northern District of Georgia, "Former Corporate CEO Sentenced to Over 6 Years in Federal Prison for "Pump and Dump" Securities Fraud Scheme", Feb. 17, 2006.*
S.C. Johnson & Son, Inc., Allercare Mold & Mildew Allergen Treatment, Notice of Proposed and Final Decisions and Directors Finding, Department of Pesticide Regulation, Pesticide Registration Branch, Aug. 13, 2001, p. 1-10.*
North Carolina Department of Agriculture and Consumer Services Pesticide Section, Pesticide Registrations, "Active Ingredients in Allercare Mold & Mildew Allergen Treatment [4822-484]", 2002.*
International Search Report for PCT/US2006/04034 dated Aug. 7, 2006.

* cited by examiner

*Primary Examiner* — John Pak
*Assistant Examiner* — Nathan W Schlientz
(74) *Attorney, Agent, or Firm* — Tim Tingkang Xia, Esq.; Morris, Manning & Martin, LLP

(57) ABSTRACT

The present invention provides a composition having disinfectancy & residual antimicrobial activity, where the antimicrobial composition comprises an organosilane quaternary compound and a quaternary ammonium compound and other formulations. Also provided are methods of disinfecting an article or providing an antimicrobial coating to an article using the same.

8 Claims, 1 Drawing Sheet

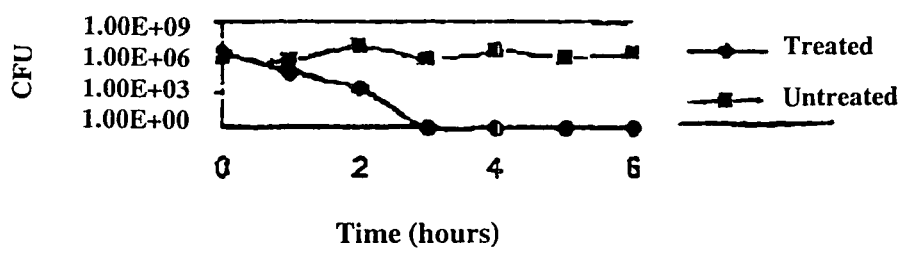
Quaternary Amine Treated and
Untreated Fabric tested against Staphylococcus
aureus using ASTM E2180
A
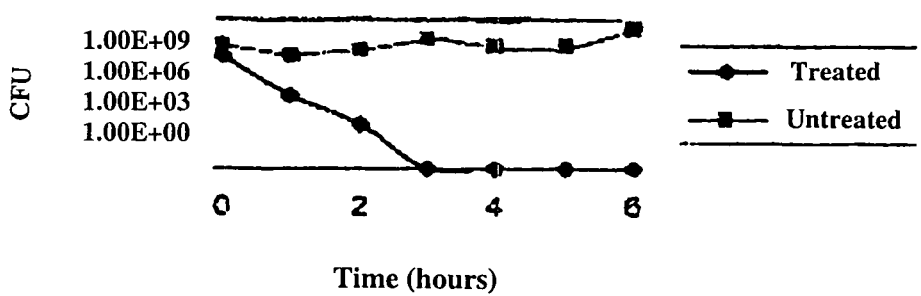
Quaternary Amine Treated and Untreated
Fabric tested against Klebsiella pneumonia
using ASTM E2180
B

METHODS AND COMPOSITIONS FOR BIOCIDAL TREATMENTS

RELATED APPLICATIONS

The present application claims the priority of U.S. Provisional Patent Application No. 60/650,502, filed Feb. 7, 2005, which is herein incorporated in its entirety.

FIELD OF THE INVENTION

The present invention relates to antimicrobial compositions comprising organosilane quaternary compounds and quaternary ammonium compounds, and applications and methods of treating surfaces and materials utilizing the same.

BACKGROUND OF THE INVENTION

Humans, animals, and plants are exposed to many surfaces and/or materials that have pathological microbial organisms present, or that may become contaminated with pathological microbial organisms. For example, humans or animals may be exposed to surfaces/materials that are in contact with household contaminating organisms, stormwater, industrial runoff, human and animal waste, and thus contaminated by pathological microbial organisms, such as, *Pseudomonas aeruginosa, Staphyloccus aureus, Escherichia coli, Shigella*, avian influenza virus H5N1, and enteroviruses. Relatively small number of these pathogens, such as *P. aeruginosa*, may cause severe health problems simply through water contact. In another example, the presence of enteroviruses is of serious concern since very small virus concentrations are capable of producing infections or diseases.

Biocides are chemical compositions that are widely used in industry for disinfection and to prevent microbiological contamination and deterioration of commercial products, materials and systems. Of the biocides presently available, alcohol, peroxides, phenol, quaternary ammonium salts, and chlorine-based biocides are widely used. However, each of these biocides has various drawbacks or disadvantages, such as, in the areas of environmental toxicity, biodegradability, corrosiveness, or physical and chemical stability.

Therefore, there is a need for compositions for the treatment of surfaces/materials that are stable, durable with a long lasting effect, relatively safe, and capable of controlling or killing a broad spectrum of biological agents, including viruses, bacteria, fungi, and other microbial agents, which do not require immiscible materials or oil in water emulsion compositions.

SUMMARY OF THE INVENTION

The present invention provides a composition having antimicrobial activity, where the antimicrobial composition comprises an organosilane quaternary compound and a quaternary ammonium compound, and where the quaternary ammonium compound is not an organosilane quaternary compound.

In one embodiment, the organosilane quaternary compound is a compound having formula $R_nSiX_{(4-n)}$, wherein (1) R is, independently, an alkene group, an alkyl group, or an alkyne group, and (2) X is, independently, an alkoxy group; and where each of the alkene group, the alkyl group, the alkyne group, and the alkoxy group optionally comprises an amino, a chloro, an epoxy, or a mercapto substituent.

In another embodiment, the quaternary ammonium compound comprises at least one compound selected from the group consisting of mono-long-chain, tri-short-chain, tetraalkyl ammonium compounds; di-long-chain, di-short-chain, tetraalkyl ammonium compounds; and trialkyl, monobenzyl ammonium compounds.

In yet another embodiment, the ratio of organosilane quaternary compound to quaternary ammonium compound may be in a weight range of about 1:100 to about 100:1.

The antimicrobial composition of the present invention may further comprise an oxidizing agent (e.g., hydrogen peroxide, an oxidizing agent such as chlorine or dioxide), a chelating agent (e.g., ethylenediaminetetraacetic acid (EDTA) or a salt thereof), or a stabilizing agent (e.g., sucrose, pentaerythritol, glycol ether, ethanol, or propelyne carbonate). The antimicrobial composition may also comprise other ingredients depending on the application and particular formulation needs and include, but are not limited to, wetting/dispensing agents, propellants, liquefied gases, surfactants, and other formulation components.

Also provided are methods of disinfecting a surface or material or providing an antimicrobial coating to a surface or substrate using the same. Methods also comprise making and using aqueous biocidal compositions for cleaning and disinfecting solid (e.g., solid of hard or soft surfaces or materials), including those which may be typically contacted by humans or animals, and providing long lasting biostatic protection. Methods also comprise providing compositions taught herein for treating, saturating, or impregnating materials or fibers such as paper, concrete additives, cellulose, fiberfill, fiberglass, polyurethane foam, textiles or non-woven fabrics thus, aiding in preventing attachment, colonization or infection and reinfection by microorganisms. The methods of the present invention may also comprise any methods for applying the compositions taught herein to a surface or space for disinfection or removal or microbes, including, without limitation, spraying, dipping, painting, dusting, wiping, dabbing, swabbing, fogging, or misting. In addition, methods also comprise formulating disinfectant and/or antimicrobial compositions for use on human or animal bodies including, but not limited to, cleaners, softeners, body lotions for bodily surfaces (e.g., skin, hands and face, hair), for example, to treat acne vulgaris and ringworm, liquid soaps, moist or dry towelettes, gels, hair shampoo, hair conditioner, deodorizers, antiperspirants, and other personal care products (see, e.g., U.S. Pat. Nos. 4,908, 355 and 4,567,039).

A composition of the present invention may have the following ingredients:
  a. An organosilane quaternary ammonium compound (OS-QAC), for example, in a range from about 0.01% to about 42%;
  b. A quaternary ammonium compound (QAC) (for example), from about 0.01% to about 32%;
  c. Water, as needed, from about 60% to about 99%; optionally;
  d. Stabilizer (for example, solvents, polyols, glycol ethers, etc.) and other ingredients as needed for the desired application of the composition, such as, other formulations apparent to those skilled in the art.

Other features and advantages of the present invention will become apparent from the following detailed description. It should be understood, however, that the detailed description and the specific examples, while indicating the preferred embodiments of the invention, are given by way of illustration only, since various changes and modifications within the spirit and scope of the invention will become apparent to those skilled in the art from this detailed description

DESCRIPTION OF THE FIGURES

FIGS. 1A and B are graphs showing material treated with the compositions of the present invention and the effect on bacteria.

DETAILED DESCRIPTION OF THE INVENTION

As used herein and in the appended claims, the singular forms "a," "an," and "the" include plural references, unless the content clearly dictates otherwise. Thus, for example, reference to "a stabilizer agent" includes a plurality of such stabilizer agents and equivalents thereof known to those skilled in the art, and reference to "the chelating agent" is a reference to one or more chelating agents and equivalents thereof known to those skilled in the art, and so forth. All publications, patent applications, patents, and other references mentioned herein are incorporated by reference in their entirety.

The present invention provides antimicrobial or biocide compositions, and methods of using the same, where the antimicrobial compositions have at least one desirable feature, such as, stable, durable with a long lasting effect, relatively safe and non-toxic, and capable of controlling or killing a broad spectrum of biological/pathological agents, including viruses, bacteria, fungi, and other microbial agents and rendering the surfaces and materials treated capable of continuing to kill or control a broad range of microbial agents.

In one aspect, the antimicrobial composition comprises an organosilane quaternary compound (OSQAC) and a quaternary ammonium compound (QAC), where the quaternary ammonium compound is not an organosilane quaternary compound.

The organosilane quaternary compound may be any suitable organosilanes known to one skilled in the art, including, without limitation, the organosilanes taught by U.S. Pat. Nos. 5,954,869; 5,959,014; 6,120,587; 6,113,815; 6,469,120; 6,221,944; 6,607,717 and 6,762,172, and U.S. patent application Ser. No. 10/392,746. In one embodiment, the organosilane quaternary compound may include, without limitation, an organosilane compound of formula $R_nSiX_{(4-n)}$, where, n is an integer of from 0 to 3;

R is, independently, an alkene group, an alkyl group, or an alkyne group; and

X is, independently, an alkoxy group.

Each of the alkene group, the alkyl group, the alkyne group, and the alkoxy group may optionally comprise an amino, a chloro, an epoxy, or a mercapto substituent. In another embodiment, the organosilane quaternary compound may be an organosilane quaternary amine compound of the following formula:

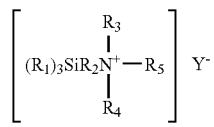

wherein, each $R_1$ is, independently, halogen or $R_6O$, where $R_6$ is H, alkyl of from about 1 to about 6 carbon atoms, unsubstituted or substituted, preferably from 1 to about 2 carbon atoms and more preferably 1 carbon atom, or acetyl- or other acyl, including substituted acyl and acyloxy; or $R_6O$ may be derived from any hydroxylated polymer, hydroxylated liquid, or hydroxylated solid regardless of water solubility; or $R_6O$ may be derived from any polyglycol such as, but not limited to, polyethyleneglycols or polypropyleneglycols, such as poly(propyleneglycol)triol (glycerol propoxylate);

$R_2$ is unsubstituted or substituted benzyl- or an unsubstituted or substituted alkyl of from about 1 to about 3 carbon atoms, preferably alkyl of from 1 to 3 carbon atoms;

$R_3$ and $R_4$ are, independently, lower alkoxy of from about 1 to about 4 carbon atoms, preferably of 2 carbon atoms, such as $CH_2CH_2OH$, $CH_2CH(OH)CH_3$; alkyl of from about 1 to about 22 carbon atoms, preferably from 1 to about 10 carbon atoms and more preferably from 1 to 2 carbon atoms; or $R_3$ and $R_4$ may, together, form a morpholine or other cyclic or heterocyclic, unsaturated or saturated, five to seven-membered ring of the formula:

—$R_3$—$(R_7)_k$—$R_4$— where k is an integer from 0 to 2 and $R_7$, where the ring is saturated, is $CH_2$, O, S, NH, $NH_2^+$, $NCH_2CH_2NH_2$, $NCH_2CH_2NH_3^+$, $NCH_2CH_2N(R_8)(R_9)$, $NCH_2CH_2N^+(R_8)(R_9)(R_{10})$, N(alkyl), N(aryl), N(benzyl), and $R_7$, where the ring is unsaturated is, N, $N^+H$, $N^+$(alkyl), $N^+$(aryl), $N^+$(benzyl), N—$CH_2$—N, $N^+H$—$CH_2$—N, $N^+$(alkyl)-$CH_2$—N, $N^+$(aryl)-$CH_2$—N, or $N^+$(benzyl)-$CH_2$—N, where $R_8$, $R_9$, and $R_{10}$ are, independently, benzyl, polyglycol, lower alkyl alcohol of from about 1 to about 4 carbon atoms, lower alkoxy of from about 1 to about 4 carbon atoms, or alkyl of from about 1 to about 22 carbon atoms, preferably 1 to about 10 carbon atoms;

$R_5$ is $CH_2C_6H_5$, $CH_2CH_2OH$, $CH_2CH(OH)CH_3$, a polyglycol (e.g., a polyethyleneglycol, a polypropyleneglycol, or an alkylated polyoxyethylene); or $R_5$ is alkyl or perfluoroalkyl of from about 1 to about 22 carbon atoms, preferably from about 12 to about 20 carbon atoms and more preferably from 14 to about 18 carbon atoms; and Y is halogen (such as Cl, Br, I), acetate, sulfate, tosylate or carboxylate, polycarboxylate salts, alcoholates, functionalized carboxylate, such as trifluoroacetate and perfluoroalkylcarboxylates, or other alkyl and arylsulfonate salts, including trifluoromethylsulfonate and anionic metal oxides, perfluoroalkylsulfonate salts, phosphate and phosphonate salts, borate and boronate salts, and benzoates or any other suitable anionic moiety.

As used herein, the term "alkyl" refers to a branched or unbranched saturated hydrocarbon group of about 1 to about 24 carbon atoms, such as methyl (Me), ethyl (Et), n-propyl, isopropyl, n-butyl, isobutyl, t-butyl, octyl, decyl, tetradecyl, hexadecyl, eicosyl, tetracosyl, and the like. The term "lower alkyl" intends an alkyl group of from about 1 to about 6 carbon atoms, preferably from 1 to 4 carbon atoms. The term "cycloalkyl" intends a cyclic alkyl group of from about 3 to about 8, preferably 5 or 6 carbon atoms. "Lower alkyl alcohol" refers to lower alkyl having attached thereto one or more hydroxy moieties, such as, but not limited to, $CH_2CH_2OH$, $CH_2CH(OH)CH_3$, $CH_2OH$, $CH_2CH_2CH_2OH$, $CH_2CH_2CH(OH)CH_3$, $CH_2CH_2CH(OH)CH_2OH$, or $CH_2CH(OH)CH(OH)CH_3$.

As used herein, the term "acyl" refers to organic acid derived moieties of the formula RCOX where R is an organic molecule and X, instead of being hydroxy, is replaced with another substituent, preferably, a suitable anion, such as a halogen including, but not limited to, F, Cl, Br, or I.

The term "alkoxy" as used herein intends an alkyl group bound through a single, terminal ether linkage; that is, an alkoxy group may be defined as OR where R is alkyl as defined above. A "lower alkoxy" group intends an alkoxy group containing from about 1 to about 6, preferably, from 1 to 4, carbon atoms. "Polyether" refers to a compound or moiety possessing multiple ether linkages, such as, but not limited to, polyethylene glycols or polypropylene glycols. "Polyalkylethers" refers to alkyls interconnected by or otherwise possessing multiple ether linkages.

The term "aryl" as used herein refers to a compound or moiety whose molecules have a ring or multiple ring structure characteristic of compounds, such as, benzene, naphthalene, phenanthrene, anthracene, i.e., either the six-carbon ring of benzene or the condensed six-carbon rings of the other aromatic derivatives, including, but not limited to phenyl, benzyl, naphthyl, benzylidine, xylil, styrene, styryl, phenethyl, phenylene, and benzenetriyl. As used herein, the term "aromatic" refers to the group of unsaturated cyclic hydrocarbons, typified by benzene, having a 6-carbon ring containing three double bonds or multiple attached benzene rings. Moreover, certain five membered cyclic compounds, such as furan (heterocyclic), are analogous to aromatic compounds. "Aromatics" include the cyclic compounds based upon a benzene functionality, as specified for aryl above. Moreover, the term "cyclic" is used to refer to all aliphatic or aromatic hydrocarbons having one or more closed rings, whether unsaturated or saturated. When used with respect to cyclic compounds or moieties, the term "unsaturated" refers to such compound or moiety possessing at least one double or triple bond or otherwise constituting an aromatic compound or moiety. Moreover, the term "saturated" refers to compounds or moieties possessing no double or triple bonds, i.e., where all available valence bonds of an atom, especially carbon, are attached to other atoms.

The term "heteroaryl" refers to an aryl where one or more of the carbon atoms of a ring have been substituted with a heteroatom, including, but not limited to, O, N, or S. Similarly, the term "heterocyclic" refers to a cyclic compound or moiety where one or more of the carbon atoms of the ring has been substituted with a heteroatom, including, but not limited to, O, N, or S.

As used herein, the term "perfluoro" or "perfluoro-analog" refers to a hydrocarbon where the hydrogen atoms attached to carbons have been replaced with F atoms. Preferably, but not necessarily, in perfluoro-analogs, most if not all of the H atoms are replaced with F atoms. A fluoro analog is contemplated to indicate a hydrocarbon where at least one hydrogen atom attached to a carbon is replaced with an F atom.

As used herein, especially in reference to alkyl and alkoxy, the term "lower" refers to a moiety having from about 1 to about 6 carbon atoms, preferably 1 to 4 carbon atoms.

As used herein, "substituted" is used to refer, generally, to a carbon or suitable heteroatom having a hydrogen or other atom removed and replaced with a further moiety. In one embodiment, halogen, hydroxy, and nitrogen based substitutions of hydrocarbon hydrogens are contemplated as within the scope of the present invention for the claimed structures. Moreover, it is intended that substituted refer to substitutions which do not change the basic and novel utility of the underlying compounds, products or compositions of the present invention. "Unsubstituted" refers to a structure wherein the reference atom does not have any further moieties attached thereto or substituted therefor.

As used herein, "branched" is used to refer, generally, to a moiety having a carbon chain backbone, e.g., alkyl or alkoxy, wherein the backbone may contain one or more subordinate carbon chain branches. For example, isobutyl, t-butyl, isopropyl, $CH_2CH_2C(CH_3)(H)CH_2CH_3$, $CH_2C(CH_2CH_3)(H)CH_2CH_3$, $CH_2CH_2C(CH_3)_2CH_3$, and $CH_2CH_2C(CH_3)_3$ would all be considered branched moieties. Moreover, it is intended that branched variations of the moieties herein described refer to variations which do not change the basic and novel utility of the underlying compounds, products or compositions of the present invention. "Unbranched" refers to a structure wherein the carbon chain does not have any branches thereon, i.e., where the carbon chain extends in a direct line.

As used herein, the term "suitable" is used to refer a moiety which is compatible with the compounds, products, or compositions as provided herein for the stated purpose. Suitability for the stated purpose may be determined by one of ordinary skill in the art using only routine experimentation.

As used herein, "optional" or "optionally" means that the subsequently described event or circumstance may or may not occur, and that the description includes instances where the event or circumstance occurs and instances where it does not. For example, the phrase optionally substituted lower alkyl means that the lower alkyl group may or may not be substituted and that the description includes both unsubstituted lower alkyl and lower alkyl where there is substitution.

By the term "effective amount" of a compound, product, or composition as provided herein is meant a sufficient amount of the compound, product or composition to provide the desired result. The exact amount required will vary from substrate to substrate, depending on the particular compound, product or composition used, its mode of administration, and the like, and it is not always possible to specify an exact effective amount. However, an appropriate effective amount may be determined by one of ordinary skill in the art using routine experimentation.

As used herein, "substrate" or "article" refers to any article, product, material, or surface that may be treated with the inventive compositions. Suitable substrates or articles are generally characterized in preferably having a negatively charged surface of oxygen atoms, or any surface capable of electrostatically, ionically or covalently adhering or binding to the compounds, products, or compositions of the present invention. The adhering or binding may occur at the silicon atom of the organosilane portion of the compounds, products, or compositions of the present invention, but such binding is not a requirement. Therefore, as used herein, the term "adhere" is meant to refer to ionic, covalent, electrostatic, or other chemical or physcial attachment of a compound, product or composition to a substrate.

Examples of organosilanes and organosilanes quaternary ammonium chlorides (OSQAC) suitable for the purposes of the present invention include, but are not limited to:

3-(trimethoxysilyl)propyldimethyloctadecyl ammonium chloride, 3-(trimethoxysilyl)propylmethyldi(decyl)ammonium chloride, 3-(trihydroxysilyl)propyl-dimethyloctadecyl ammonium chloride, octadecyltrimethoxysilane, perfluorooctyltriethoxysilane, aminoethylaminopropyltrimethoxysilane, 3-aminopropyltrimethoxysilane, 3-aminopropyltriethoxysilane, 3-chloropropyltrimethoxysilane, 3-chloropropyltriethoxysilane, 3-chloropropyltrichlorosilane, 3-glycidoxypropyltrimethoxysilane, 3-glycidoxypropyltriethoxysilane, 3-methacryloxypropyltriethoxysilane, 3-methacryloxypropyltrimethoxysilane, methyldichlorosilane, sodium(trihydroxysilyl)propylmethylphosphonate, trichlorosilane, n-2-vinylbenzylamino-ethyl-3-aminopropyltrimethoxysilane HCL,
vinyltriacetoxysilane,
vinyltrimethoxysilane,
vinyltriethoxysilane,
vinyltrichlorosilane,
dimethyldichlorosilane,
dimethyldimethoxysilane,
diphenyldichlorosilane,
ethyltrichlorosilane,
ethyltrimethoxysilane,
ethyltriethoxysilane,
isobutyltrimethoxysilane,
n-octyltriethoxysilane,
methylphenyldichlorosilane,
methyltrichlorosilane,
methyltrimethoxysilane,
phenyltrichlorosilane,
phenyltrimethoxysilane,
n-propyltrichlorosilane,
n-propyltrimethoxysilane,
silicon tetrachloride,
decyltrichlorosilane,
dichloromethyl(4-methylphenethyl)silane,
diethoxymethylphenylsilane,
[3-(diethylamino)propyl]trimethoxysilane,
3-(dimethoxymethylsilyl)-1-propanethiol,
dimethoxymethylvinylsilane,
3-[tris(trimethylsilyloxy)silyl]propyl methacrylate,
trichloro[4-(chloromethyl)phenyl]silane,
methylbis(trimethylsilyloxy)vinylsilane,
methyltripropoxysilane,
trichlorocyclopentylsilane,
$(CH_3O)_3Si(CH_2)_3N^+(CH_3)_2C_{18}H_{37}Cl^-$,
$(CH_3O)_3Si(CH_2)_3N^+(CH_3)_2C_{18}H_{37}Br^-$,
$(CH_3O)_3Si(CH_2)_3N^+(C_{10}H_{21})CH_3Cl^-$,
$(CH_3O)_3Si(CH_2)_3N^+(C_{10}H_{21})CH_3Br^-$,
$(CH_3O)_3Si(CH_2)_3N^+(CH_3)_3Cl^-$,
$(CH_3O)_3Si(CH_2)_3N^+(CH_3)_2C_8H_{17}Cl^-$,
$(CH_3O)_3Si(CH_2)_3N^+(CH_3)_2C_{10}H_{21}Cl^-$,
$(CH_3O)_3Si(CH_2)_3N^+(CH_3)_2C_{12}H_{25}Cl^-$,
$(CH_3O)_3Si(CH_2)_3N^+(CH_3)_2C_{14}H_{29}Cl^-$,
$(CH_3O)_3Si(CH_2)_3N^+(CH_3)_2C_{16}H_{33}Cl^-$,
$(CH_3O)_3Si(CH_2)_3N^+(CH_3)_2C_{20}H_{41}Cl^-$,
$(CH_3O)_3Si(CH_2)_3N^+(CH_4H_9)_3Cl^-$,
$(CH_3O)_3Si(CH_2)_3N^+(C_2H_5)_3Cl^-$,
$(CH_3CH_2O)_3Si(CH_2)_3N^+(CH_3)_2C_{18}H_{27}Cl^-$,
$(CH_3O)_3Si(CH_2)_3N^+(CH_3)_2(CH_2)_3NHC(O)(CH_2)_6CH_3Cl^-$,
$(CH_3O)_3Si(CH_2)_3N^+(CH_3)_2(CH_2)_3NHC(O)(CH_2)_8CH_3Cl^-$,
$(CH_3O)_3Si(CH_2)_3N^+(CH_3)_2(CH_2)_3NHC(O)(CH_2)_{10}CH_3Cl^-$,
$(CH_3O)_3Si(CH_2)_3N^+(CH_3)_2(CH_2)_3NHC(O)(CH_2)_{12}CH_3Cl^-$,
$(CH_3O)_3Si(CH_2)_3N^+(CH_3)_2(CH_2)_3NHC(O)(CH_2)_{14}CH_3Cl^-$,
$(CH_3O)_3Si(CH_2)_3N^+(CH_3)_2(CH_2)_3NHC(O)(CH_2)_{16}CH_3Cl^-$,
$(CH_3O)_3Si(CH_2)_3NHC(O)(CF_2)_6CF_3$,
$(CH_3O)_3Si(CH_2)_3NHC(O)(CF_2)_8CF_3$,
$(CH_3O)_3Si(CH_2)_3NHC(O)(CF_2)_{12}CF_3$,
$(CH_3O)_3Si(CH_2)_3NHC(O)(CF_2)_{14}CF_3$,
$(CH_3O)_3Si(CH_2)_3NHC(O)(CF_2)_{16}CF_3$,
$(CH_3O)_3Si(CH_2)_3NH SO_2(CF_2)_7CF_3$,
$(CH_3O)_3Si(CH_2)_3N^+(CH_3)_2(CH_2)_3NHC(O)(CF_2)_6CF_3$,
$(CH_3O)_3Si(CH_2)_3N^+(CH_3)_2(CH_2)_3NHC(O)(CF_2)_8CF_3$,
$(CH_3O)_3Si(CH_2)_3N^+(CH_3)_2(CH_2)_3NHC(O)(CF_2)_{10}CF_3^-$,
$(CH_3O)_3Si(CH_2)_3N^+(CH_3)_2(CH_2)_3NHC(O)(CF_2)_{12}CF_3$,
$(CH_3O)_3Si(CH_2)_3N^+(CH_3)_2(CH_2)_3NHC(O)(CF_2)_{14}CF_3$,
$(CH_3O)_3Si(CH_2)_3N^+(CH_3)_2(CH_2)_3NHC(O)(CF_2)_{16}CF_3$,
$(CH_3O)_3Si(CH_2)_3N^+(CH_3)_2(CH_2)_3NHC(O)(CF_2)_7CF_3$,
$(CH_3O)_3Si(CH_2)_3N^+(CH_3)_2(CH_2)_3NHSO_2(CF_2)_9CF_3$,
$(CH_3O)_3Si(CH_2)_3N^+(CH_3)_2(CH_2)_3NHSO_2(CF_2)_7CF_3$,
$(CH_3O)_3Si(CH_2)_3N^+(CH_3)_2(CH_2)_3NHSO_2(CF_2)_{11}CF_3$,
$(CH_3O)_3Si(CH_2)_3N^+(CH_3)_2(CH_2)_3NHSO_2(CF_2)_{13}CF_3$,
$(CH_3O)_3Si(CH_2)_3N^+(CH_3)_2(CH_2)_3NHSO_2(CF_2)_{15}CF_3$,
and
$(CH_3O)_3Si(CH_2)_3N^+(CH_3)_2(CH_2)_3NHSO_2(CF_2)_{16}CF_3$.

In an embodiment, the organosilane quaternary ammonium compound may be 3-trimethoxysilyl propyltetradecyldimethyl ammonium chloride, 3-trimethoxysilyl propyldidecylmethyl ammonium chloride, or 3-trihydroxysilyl propyloctadecyl ammonium chloride. In an embodiment, the antimicrobial composition of the present invention may contain organosilane quaternary compounds in a concentration range of about 0.01-10% by weight, more preferably about 0.01-2%. Two commercially relevant examples of organosilane quaternary compounds are SiS AM7200 (72% active) and Dow Corning 5700 (42% active) manufactured by SiShield Technologies, Inc., Atlanta, Ga. and Dow Corning Corporation, Midland, Mich., respectively.

The compositions of the present invention may comprise OSQAC in a range of from about 0.01% to about 42%, from about 0.01% to about 32%; from about 0.01% to about 25.0%; from about 0.01% to about 22%; from about 0.01% to about 12%; from about 0.01% to about 10%; from about 0.01% to about 6.0%; from about 0.01% to about 5.0%; from about 0.01% to about 4.0%; from about 0.01% to about 3.0%; from about 0.01% to about 2.0%; from about 0.01% to about 1.0%; from about 0.01% to about 0.1%; from about 1.0% to about 42%; from about 10% to about 42%; from about 20% to about 42%; and from about 30% to about 42%. The OSQAC may be about 72% active as made, such as the Sishield product above, as this activity is commonly understood by those skilled in the art, or the OSQAC may be about 42%, such as the DOW product above, or the OSQAC may have any active amount that is capable of being formed during synthesis. The compositions of the present invention may comprise QAC, which may comprise an individual type or one QAC or a mixture or combination of different QACs in a range of from about 0.01% to about 32%; from about 0.01% to about 28%; from about 0.01% to about 25.0%; from about 0.01% to about 22%; from about 0.01% to about 12%; from about 0.01% to about 10%; from about 0.01% to about 6.0%; from about 0.01% to about 5.0%; from about 0.01% to about 4.0%; from about 0.01% to about 3.0%; from about 0.01% to about 2.0%; from about 0.01% to about 1.0%; from about 0.01% to about 0.1%; from about 1.0% to about 32%; from about 10% to about 32%; from about 20% to about 32%; and from about 28% to about 32%.

The one or more QAC quaternary ammonium compounds may be any quaternary ammonium compound suitable for the purposes of the present invention known to a person skilled in the art, including, without limitation, mono-long-chain, tri-short-chain, tetraalkyl ammonium compounds; di-long-chain, di-short-chain, tetraalkyl ammonium compounds; and trialkyl, mono-benzyl ammonium compounds. Examples of such quaternary ammonium compounds include, without limitation, the Bardac series compounds such as BARDAC® MB 2050 (N,N-Dialkyl($C_{8-10}$)-N—N-dimethyl ammonium, 40% ethanol/10% water), made by Lonza, Lonza compounds and product series such as 208M (32% Alkyl ($C_{14}$ 50%, $C_{12}$ 40%, $C_{16}$ 10%) Dimethyl benzyl ammonium chloride, 24% octyl decyl dimethyl ammonium chloride, 9.6% Dioctyl dimethyl ammonium chloride, 14.4% Didecyl dimethyl ammonium chloride, 10% ethyl alcohol, and 10% water), and Stepan Co. product series and compounds such as BTC 2125. For example, QAC may comprise BTC® 1010 Didecyl dimethyl ammonium chloride; BTC® 1010-80% Didecyl dimethyl ammonium chloride; BTC® 1218-50 Alkyl dimethyl benzyl ammonium chloride (<10% $C_8+C_{10}$, 50% $C_{12}$, 19% $C_{14}$, 9% $C_{16}$, 8% $C_{18}$); BTC® 1218-80E Alkyl dimethyl benzyl ammonium chloride (<10% $C_8+C_{10}$, 50% $C_{12}$, 19% $C_{14}$, 9% $C_{16}$, 8% $C_{18}$); BTC® 2050 Didecyldimethyl ammonium chloride; BTC® 2125M n-Alkyl dimethyl benzyl ammonium chlorides (and) n-Alkyl dimethyl ethylbenzyl ammonium chlorides; BTC® 2125M P40 n-Alkyl dimethyl benzyl ammonium chlorides and n-Alkyl dimethyl ethylbenzyl ammonium chlorides; BTC® 2125M 80% n-Alkyl dimethyl benzyl ammonium chlorides and n-Alkyl dimethyl ethylbenzyl ammonium chlorides; BTC® 2125M 90% n-Alkyl dimethyl benzyl ammonium chlorides and n-Alkyl dimethyl ethylbenzyl ammonium chlorides; BTC® 50 n-Alkyl dimethyl benzyl ammonium chloride; BTC® 65 n-Alkyl dimethyl benzyl ammonium chloride; BTC® 818 Dialkyl dimethyl ammonium chloride; BTC® 818 80% Dialkyl dimethyl ammonium chloride; BTC® 824 n-Alkyl dimethyl benzyl ammonium chloride; BTC® 8248 n-Alkyl dimethyl benzyl ammonium chloride; BTC® 8249 n-Alkyl dimethyl benzyl ammonium chloride; BTC® 835 n-Alkyl dimethyl benzyl ammonium chloride; BTC® 8358 n-Alkyl dimethyl benzyl ammonium chloride; BTC® 885 n-Alkyl dimethyl benzyl ammonium chloride and Dialkyldimethyl ammonium chloride; BTC® 888 n-Alkyl dimethyl benzyl ammonium chloride and Dialkyl dimethyl ammonium chloride; BTC® D 80 Alkyl dimethyl benzyl ammonium chloride (<10% $C_8+C_{10}$, 50% $C_{12}$, 19% $C_{14}$, 9% $C_{16}$, 8% $C_{18}$).

In one embodiment, the quaternary ammonium compound may further comprise a chloride or a saccharinate counterion, or a combination thereof. In another embodiment, the composition of the present invention may contain quaternary ammonium compounds in a concentration range of about 0.01-5%, or about 0.1-2%. In still another embodiment, the composition of the present invention may comprise a ratio of organosilane quaternary compound to quaternary ammonium compound in a weight range of about 1:100 to about 100:1, such as, without limitation, about 1:10, about 1:20, about 1:30, about 1:40, about 1:50, about 1:60, about 1:70, about 1:80, about 1:90, about 90:1, about 80:1, about 70:1, about 60:1, about 50:1, about 40:1, about 30:1, about 20:1, about 10:1, and any suitable ratio in between. In an embodiment, the ratio may be in a weight range of about 1:10 to about 10:1. The exact ratio of organosilane quaternary compound to quaternary ammonium compound will be determined by, for instance, the type of organosilane quaternary compound and quaternary ammonium compound used in the composition, the particular use and surface or material to which the composition is applied, as well as the specific nature of the microorganism contamination or potential microorganism contamination. The ratio of these compounds to use would be readily determinable by one skilled in the art.

The compositions of the present invention may further comprise one or more of an oxidizing agent, a chelating agent, a surfactant, a softener, a detergent, a binder, a wetting agent, a fragrance, a scent, a dye, an antimigrant, an antifoaming agent, and/or a stabilizing agent.

The oxidizing agent may be any oxidizing agent suitable for use in a biocide or in an antimicrobial composition known to one skilled in the art. Examples of oxidizing agent include, without limitation, hydrogen peroxide, chlorine-based oxidizing agent (e.g., chlorine, chlorine dioxide, sulfur dioxide, oxygen, ozone), and a bromine-based oxidizing agent. In one embodiment, the oxidizing agent may be hydrogen peroxide. In another embodiment, the composition of the present invention may contain hydrogen peroxide in a concentration range of about 1-5%, or about 1.8-2.2%.

Chelating agents of the present invention may include inorganic or organic compounds. The chelating agent used may depend upon the specific application. Application specific concerns include, e.g., cost, nature of the metal ions to be chelated, compatibility with the components of the composition, and solubility in the composition. Chelating agents of the present invention are generally non-toxic to animals and humans in the amounts described herein. One skilled in the art would be able to appreciate these parameters and select the appropriate chelating agent without undo experimentation.

In one embodiment, chelating agents of the present invention may have a complex formation equilibrium constant of about $10^7$ to about $10^{27}$. In another embodiment, the chelating agent used in the composition may have a complex formation constant of about $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, $10^{20}$, $10^{21}$, $10^{23}$, $10^{24}$, $10^{25}$, $10^{26}$, and $10^{27}$.

A safe and effective amount of one or more chelating agents may be added to the compositions of the present invention, and when present comprising about 0.1% to about 10% by weight of the composition. In one embodiment, the composition may comprise from about 1% to about 5% by weight of chelating agents. In another aspect, the biocidal composition may comprise, by weight, about 0.50%, 0.75%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, and 5.0% of chelating agents.

Exemplary chelating agents of the present invention include, without limitation, carboxylic acids, polycarboxylic acids, amino acids and phosphates, such as, acetic acid, adenine, adipic acid, alanine, albumin, arginine, ascorbic acid, asparagines, aspartic acid, benzoic acid, n-butyric acid, casein, citraconic acid, citric acid, cysteine, dehydracetic acid, 3,4-dihydroxybenzoic acid, diethylenetriaminepentaacetic acid (DTPA), dimethylglyoxime, O,O-dimethylpurpurogallin, EDTA, formic acid, fumaric acid, globulin, gluconic acid, glutamic acid, glutaric acid, glycine, glycolic acid, glycylglycine, glycylsarcosine, guanosine, histamine, histidine, 3-hydroxyflavone, inosine, lactic acid, leucine, lysine, maleic acid, malic acid, methionine, methylsalicylate, ornithine, orthophosphate, oxalic acid, oxystearin, phenylalanine, phosphoric acid, phytate, pimelic acid, pivalic acid, polyphosphate, praline, propionic acid, purine, pyrophosphate, pyruvic acid, riboflavin, salicylaldehyde, salicyclic acid, sarcosine, serine, sorbitol, succinic acid, tartaric acid, tetrametaphosphate, thiosulphate, threonine, trimetaphosphate, triphosphate, tiyptophani, uridine diphosphate, uridine triphosphate, n- valeric acid, valine, xanthosine, and salts, combinations, or complexes thereof.

Chelating agents suitable for the purposes of the present invention may also include, but are not limited to, ethylenediamine tetraacetic acid (EDTA) or its salts (e.g. EDTA sodium salt), phosphonates, nitrilotriacetic acid (NTA) or its salts, hydroxyethylene diamine and triacetic acid (HEDTA) or its salts, diethylene triamine pentaacetic acid (DTPA) or its salts, salicylates (e.g., sodium salicylate, 5-methoxysalicylate and homovanilate), N-amino acyl derivatives of beta-diketones (enamines), triethylene tetramine dihydrochloride (TRIEN), ethylene glycol bis(2-aminoethyl ether)-N,N,N'N'- tetraacetic acid (EGTA), triethylenetetramine hexaacetic acid (TTG), deferoxamine, dimercaprol, acetoacetamide, ammonium carbamate, ammonium pyrrolidinedithiocarbamate (APDC), dimethyl malonate, methyl acetoacetate, N-methyl acetoacetamide, 2,4-pentanedione, tetramethylammonium thiobenzoate, tetramethylammonium trifluoroacetate, tetramethylthiuram disulfide (TMTDS), trifluoracetic acid, ammonium lactate, malonic acid, gamma-butyrolactone, methyldiethanolammonium trifluoroacetate, trifluoroacetic acid, and tetramethylammonium thiobenzoate.

In one embodiment, the present invention comprises a composition comprising, by weight, about 0.50%, 0.75%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, and 5.0% of EDTA and/or salts thereof.

As used herein, the term surfactant (or surface-active agent) refers to any compound which, when applied to water, a solution, a liquid, a gel, or a slurry, reduces surface tension of the composition or the mixture or the interfacial tension between water/a solvent and another solvent, or between water/a solvent and a solid. Surfactants may be classified as anionic, cationic, non-ionic, amphoteric or zwitterionic, depending on the overall charge that the molecule carries.

Examples of nonionic surfactants include, without limitation, alcohol ethoxylates, such as, $C_8$ to $C_{18}$ alcohol ethoxylates containing from about 3 to about 50 moles of ethylene oxide per molecule; $C_8$ to $C_{18}$ fatty acid esters and amides containing from about 2 to about 50 moles of ethylene oxide; $C_8$ to $C_{18}$ fatty alcohols; $C_8$ to $C_{18}$ diols, such as, tetramethyl decynediol and dimethyl octynediol; block copolymers of polyethylene oxide and polypropylene oxide; $C_8$ to $C_{18}$ fatty acid esters of glycerine; ethoxylated and propoxylated $C_8$ to $C_{18}$ fatty alcohols; $C_8$ to $C_{18}$ fatty amine and amidoamine oxides; $C_8$ to $C_{18}$ fatty amides and alkanolamides; and alkyl saccharides (e.g., alkyl glucosides) or alkenyl-saccharides.

Examples of amphoteric surfactants include, without limitation, amine oxides; $C_8$ to $C_{18}$ sultaines, such as, coco-sultaine and cocamidopropyl hydroxysultaine; $C_8$ to $C_{18}$ fatty derivatives of amino acids, such as, cocamphocarboxyglycinate and lauramphoglycinate; $C_8$ to $C_{18}$ alkyl betaines, such as, decyl betaine, coco-betaine, lauryl betaine, myristyl betaine and stearyl betaine; and $C_8$ to $C_{18}$ amidoalkyl betaines, such as, cocoamidoethyl betaine, cocamidopropyl betaine, lauramidopropyl betaine, myristamidopropyl betaine, and oleamidopropyl betaine. Sarcosine surfactants, such as, $C_8$ to $C_{18}$ alkyl sarcosines and their alkali metal or ammonium salts (e.g., sodium, potassium, lithium or ammonium $C_8$ to $C_{18}$ alkyl sarcosinates), are also contemplated by the present invention.

Examples of cationic surfactants include, without limitation, quaternary ammonium compounds which may contain at least two nitrogen-bonded alkyl chains having at least about 16 carbon atoms, such as, distearyldimonium chloride and ditallowdimonium chloride; $C_8$ to $C_{18}$ fatty alkyl amines, amidoalkylamines, and amidoalkanolamines, and their salts; ethoxylated amines; amine oxides; and immidazoline.

Examples of anionic surfactants useful in the formulations of the present invention include, without limitation, alkyl sulphates, alkyl or alkane sulphonates, linear alkyl benzene or naphthalene sulphonates, secondary alkane sulphonates, alkyl ether sulphates or sulphonates, alkyl phosphates or phosphonates, dialkyl sulphosuccinic acid esters, sugar esters (e.g., sorbitan esters), $C_8$ to $C_{18}$ alkyl glucosides, alkyl carboxylates, paraffin sulphonates sulphosuccinate esters, and sulphated linear alcohols.

The surfactant may optionally be present in the composition of the present invention in amounts of from about 0% to about 30% by weight, or from about 0.1% to 15% by weight, or from about 1% to about 10%, or from about 2.0% to about 4.0% by weight.

The stabilizing agent suitable for the purposes of the present invention may include any stabilizer which is capable of stabilizing the organosilanes of the present invention by preventing, reducing, or inhibiting self-condensation or other inactivation of the compounds and products and optionally, simplifying the storage, transportation, and/or dilution (e.g., with water) of the composition. In one embodiment, the stabilizing agent may be a sucrose, pentaerythritol, ethanol, glycol ether, carbonate, such as, without limitation, the carbonate stabilizer taught in U.S. Pat. No. 6,762,172. In an embodiment, the stabilizing agent may be propylene carbonate.

In one embodiment, the present invention provides a composition comprises about 50-80% water; organosilane quaternary compounds in a concentration range of about 0.1-10%; quaternary ammonium compounds in a concentration range of about 0.01-5%; EDTA in a concentration range of about 1-5%; hydrogen peroxide in a concentration range of about 1-5%; isopropyl alcohol (IPA) in a concentration range of about 1-10%; Glycol Ether DB in a concentration range of about 1-10%; and NP-9 in a concentration range of about 1-10%. In another embodiment, the present invention provides a composition comprises about 60-70% water; organosilane quaternary compounds in a concentration range of about 3-6%; quaternary ammonium compounds in a concentration range of about 0.1-4%; EDTA at a concentration of range of about 1.8-2.2%; hydrogen peroxide at a concentration range of about 1.8-2.2%; isopropyl alcohol at a concentration range of about 5-7%; Glycol Ether DB at a concentration range of about 5-7%; and NP-9 at a concentration range of about 2-4%. In another embodiment, the present invention comprises a composition comprising about 80-98% water, SOQAC (72% Active) in concentration range of about 0.01-1%; QAC in a concentration range of about 0.01-3%; isopropyl alcohol in a concentration range of about 0.01-3%; Glycol Ether DB about 0.01-5%; Barlox about 0.01-5%; hydrogen peroxide (50%) about 0.01-2%; NP-9 in concentration of about 0.01-2%: and EDTA about 0.01-2%. Glycol Ether DB is also known as Diethylene glycol monobutyl ether (DGBE) or 2-(2-Butoxyethoxy) ethanol. Barlox is a tradename for amine oxides, made by Lonza, and these are surfactants, which may find use in a variety of markets: household cleaners, personal care products and others. NP-9 is a tradename for a nonionic surfactant, made by Dow Chemical, a nonionic surfactant, nonylphenol ethoxylate.

Compositions of the present invention comprise product formulations used for cleaning and/or disinfecting surfaces, including bodies or humans or animals, or clothing or bedding, or house hold cleaners, carpet cleaners, or cleansers for surfaces found in or around where humans or animals live or work, including but not limited to hand soaps and creams, shampoos and conditioners, household cleaning products, carpet cleaners, upholstery cleaners, laundry detergents, automobile or animal carrier cleansers, rinses, gels, and other formulations for cleaning or treating surfaces of humans or animals or surfaces that they touch or that touch them.

In another aspect, the present invention provides methods of disinfecting an article and a method of providing an antimicrobial coating to an article, including the step of contacting the article with a composition having antimicrobial activity, where the composition comprises an organosilane quaternary compound and a quaternary ammonium compound, and where the quaternary ammonium compound is not an organosilane quaternary compound.

The compositions of the present invention may be used to disinfect a surface or a material contaminated with virus or viral particles. For example, the surface may be contaminated with the highly pathogenic H5N1 avian influenza virus, among other pathogenic agents such as *Bacillus anthraces* (anthrax) and *Bacillus atrophaeus* spores. The materials and compositions of the present invention may also be used to disinfect surfaces/materials contaminated with gram positive bacteria (e.g., *Staphylococcus aureus*), gram negative bacteria (e.g., *E. Coli* and *Pseudomonas aeruginosa*), fungi (e.g., *Aspergillus niger*), yeasts (e.g., *Candida albicans*), and algae.

A variety of surfaces and materials may be treated using the compositions of the present invention, including, without limitation, surfaces and materials in commercial or industrial environments. Examples of such treatments include, but are not limited to, treatment of poultry houses including cages and equipment, farm and transportation vehicles for animals, foot and tire dips, walls, ceilings, floors, and fixtures found in food processing plants, refrigerators and coolers, surfaces found in broiler and breeder farms, hatchers, setters, evaporative coolers, humidifying systems, and ceiling fans found in hatcheries, surfaces found in zoos, emergency vehicles, homes, offices and automobiles, hotels, motels, schools, day care centers, hospitals, contagious illness rooms, and correctional facilities.

The compositions of the present invention may be applied to surfaces or materials using any means suitable for the particular purpose which is known in the art, such as, without limitation, by soaking, impregnating, mixing, painting, spraying, injecting, and via aerosols. In one embodiment, the compositions of the present invention may be used to impregnate or coat surfaces or materials to disinfect the articles and to provide durable biostatic protection against reinfection by microorganisms. Examples of such articles include, without limitation, outwear apparel, underwear and intimate apparel, hosiery and socks, bed sheets, blankets, bedspreads, curtains and draperies, carpets, rugs, throw rugs, toweling, toilet tank covers, floor and door mats, shower curtains, athletic and casual wear, athletic and casual shoes or shoe insoles, indoor and outdoor awnings including umbrellas, upholstery, vacuum cleaner bags and filters, vinyl paper-wallpaper, mattress pads and ticking, abrasive and polishing buffer pads, fire hose fabric, fiberfill, air filters, sand bags, tents, tarpaulins, sails, and ropes, multipurpose disposal wiping cloths, pre-moistened towelettes and tissue wipes, non-woven disposable diapers, non-woven materials used for personnel, masks, hats, gloves, footwear, and protective gear or gowns. In one embodiment, the compositions of the present invention may further comprise compounds and materials readily known in the art that are useful to allow the compositions of the present invention to be applied during manufacture of materials, such as, without limitation, paper, textile, and non-woven fabrics. In another embodiment, the composition of the present invention may further comprise compounds and materials readily known in the art that are useful to allow the compositions of the present invention to be applied to a finished article. For example, the compositions of the present invention may be used to treat fabrics, such as military fatigues, and are capable of preventing attachment and growth of bacteria and spores, and thus protecting the humans wearing the clothing.

The compositions of the present invention may be used to disinfect and provide a durable, long-lasting antimicrobial or biostatic coating for the treatment of wounds and injuries to humans and animals, such as, burns, skin grafts, lacerations, surgical incisions, and abrasions.

In addition, the materials and compositions of the present invention may be used to disinfect and provide a durable, long-lasting antimicrobial or biostatic coating in treatment of food materials, such as, in cleaning and preparing food in the restaurant and hospitality environment, and processing of food prior to packaging, and cleaning and disinfecting food at an intermediate step of food processing.

The following examples illustrate the present invention, which are set forth to aid in the understanding of the invention, and should not be construed to limit in any way the scope of the invention as defined in the claims.

EXAMPLES

Example 1

The antimicrobial activities of Antimicrobial Clear Coating AM100, were assayed by NAMSA, a contract testing facility at 3400 Cobb International Blvd., Kennesaw, Ga. 30152-7601. The formulation of Antimicrobial Clear Coating AM100 is listed in Table 1.

TABLE 1

| | |
|---|---|
| SiS AM7200 | 1.4% by weight |
| BARDAC 208 | 0.56% |
| Glycol Ether DB | 0.84% |
| Wetting Agent | 0.20% |
| Acrylic Binder (B F GoodRich #26345) | 0.05% |
| Water | 96.95% |

The formulation may also be an aqueous composition is made comprising SOQAC(SiShield, 72% Active) . . . 1.4% by weight, for example, 3-trimethoxysilyl propyltetradecyldimethyl ammonium chloride, 3-trimethoxysilyl propyldidecylmethyl ammonium chloride, or 3-trihydroxysilyl propyloctadecyl ammonium chloride may be used, QAC (Lonza, Bardoc 208) . . . 0.56%, which may be QAC made from one or a mixture of BTC® 2125M n-alkyl dimethyl benzyl ammonium chloride (and) n-alkyl dimethyl ethylbenzyl ammonium chloride; or Bardac 2050 (N,N-dialkyl(C8-10)_-N,N-dimethyl ammonium chloride), or Bardac 208M (alkyl dimethyl benzyl and dialkyl dimethyl ammonium chloride), and optionally, Glycol Ether DB . . . 0.84%, wetting Agent . . . 0.20%, acrylic Binder . . . 0.05% (BF GoodRich #26345), and water . . . 96.95%.

Two tongue depressors measuring 15 mm×50 mm for each organism tested were dipped into the antimicrobial clear coating and were allowed to air-dry before testing. Target Inoculum Level was 1.5-3.0×10$^5$ CFU/ml. As depicted in Table 2, the Antimicrobial Clear Coating AM100 achieved a reduction effect of more than 99.99% for both microorganisms tested.

TABLE 2

| | Organism Count (CFU/ml) | | |
|---|---|---|---|
| Sample Identification | Zero time | 24 Hour | Percent Reduction |
| *Staphylococcus aureus* ATCC 6538 -Treated | 1.7 × 10$^5$ | <10 | 99.99 |
| *Staphylococcus aureus* ATCC 6538 -Control | 1.5 × 10$^5$ | 1.6 × 10$^6$ | NR |
| *Klebsiella pneumoniae* ATCC 4352 -Treated | 1.6 × 10$^5$ | 1.6 × 10$^6$ | 99.99 |
| *Klebsiella pneumoniae* ATCC 4352 -Control | 1.5 × 10$^5$ | 4.3 × 10$^6$ | NR |

NR = No Reduction

Example 2

The sporocidal and germicidal activities of SiShield BST 3651 MSU were studied at Infectious Diseases Department, School of Veterinary Medicine, University of Buenos Aires using modified sporocidal AOAC tests. In brief, series of diluted *Bacillus anthracis* spores and vegetative forms were in contact with SiShield BST 3651 MSU for various amounts of time (e.g., 10 minutes, 30 minutes, or 60 minutes) and the effects of such exposure on the spores and vegetative forms were investigated.

The formulation of SiShield BST 3651 MSU is listed in Table 3.

TABLE 3

| | |
|---|---|
| SiS AM7200, such as 3-trimethoxysilyl propyltetradecyldimethyl ammonium chloride | 0.51%* |
| BARDAC 208 | 0.21%* |
| Barlox 12 | 0.25%* |
| IPA | 0.75%* |
| NP-9 | 0.38%* |
| EDTA (39%) | 0.38%* |
| H₂O₂ (50%) | 0.25%* |
| Water | 97.37% |

*after dilution of 1:8 using water

The study found that a 1:8 diluted SiShield BST 3651 MSU (in sterile distilled water) achieved a 99.99999% reduction in number of *Bacillus anthracis* spores and vegetative forms. In another set of experiments, such diluted SiShield composition demonstrated a 99.9999% reduction of *Bacillus anthracis* spores when sprayed on glass slides contaminated with *Bacillus anthracis* spores.

Example 3

The antimicrobial activities of SiS Textile Antimicrobial Additive were examined by the Hong Kong Standards and Testing Centre using AATCC Test Method 100-199.

The formulation of SiS Textile Antimicrobial Additive is listed in Table 4.

TABLE 4

| | |
|---|---|
| SiS AM7200 or OSQAC | 1.4% by weight |
| BARDAC 208 | 0.56% |
| Glycol Ether DB | 0.84% |
| Wetting Agent | 0.20% |
| Acrylic Binder (BF GoodRich #26345) | 0.05% |
| Water | 96.95% |

The study demonstrated that SiS Textile Antimicrobial Additive was able to eliminate 99.99% of *Aspergillus niger* (ATCC 16404), *Escherichia coli* (ATCC 25922), and *Staphylococcus aureus* (ATCC 25923) inoculated.

Example 4

The antimicrobial activities of SiS Odor Shield—Extra Strength were examined by the Hong Kong Standards and Testing Centre using AATCC Test Method 100-199.

The formulation of SiS Odor Shield—Extra Strength is listed in Table 5.

TABLE 5

| | |
|---|---|
| SiS AM7200 | 0.51%* |
| BARDAC 208 | 0.21%* |
| Barlox 12 | 0.25%* |
| IPA | 0.75%* |
| NP-9 | 0.38%* |
| EDTA (39%) | 0.38%* |
| Fragrance | 0.01%* |
| Water | 97.61% |

*after dilution of 1:8 using water

The study demonstrated that SiS Odor Shield—Extra Strength was able to eliminate 99.99% of *Aspergillus niger* (ATCC 16404), *Escherichia coli* (ATCC 25922), and *Staphylococcus aureus* (ATCC 25923) inoculated.

Example 5

The antimicrobial activities of SiS Concrete Clear Coating were examined by the Hong Kong Standards and Testing Centre using AATCC Test Method 100-199.

The formulation of SiS Concrete Clear Coating is listed in Table 6.

TABLE 6

| | |
|---|---|
| 3-trimethoxysilyl propyltetradecyldimethyl ammonium chloride | 1.4% by weight |
| BARDAC 208 | 0.56% |
| Glycol Ether DB | 0.84% |
| Wetting Agent | 0.20% |
| Acrylic Binder (BF GoodRich #26345) | 0.05% |
| Water | 96.95% |

The study demonstrated that SiS Concrete Clear Coating was able to eliminate 99.99% of *Aspergillus niger* (ATCC 16404), *Klebsiella pneumoniae* (ATCC 4352), and *Staphylococcus aureus* (ATCC 25923) inoculated.

Example 6

The antimicrobial activities of SiS Air Filter Antimicrobial were examined by the Hong Kong Standards and Testing Centre using AATCC Test Method 100-199.

The formulation of SiS Air Filter Antimicrobial is listed in Table 7.

TABLE 7

| | |
|---|---|
| SiS AM7200 | 1.4% by weight |
| BARDAC 208 | 0.56% |
| Glycol Ether DB | 0.84% |
| Wetting Agent | 0.20% |
| Acrylic Binder (BF GoodRich #26345) | 0.05% |
| Water | 96.95% |

The study demonstrated that SiS Air Filter Antimicrobial was able to eliminate 99.99% of *Aspergillus niger* (ATCC 16404), *Klebsiella pneumoniae* (ATCC 4352), and *Staphylococcus aureus* (ATCC 25923) inoculated.

Example 7

The antimicrobial activities of SiS All Purpose Cleaner Disinfectant & Bacteria Protectant were examined by the Hong Kong Standards and Testing Centre using AATCC Test Method 100-199.

The formulation of All Purpose Cleaner Disinfectant & Bacteria Protectant is listed in Table 8.

TABLE 8

| | |
|---|---|
| SiS AM7200, such as 3-trimethoxysilyl propyltetradecyldimethyl ammonium chloride | 0.51%* |
| BARDAC 208 | 0.21%* |
| Barlox 12 | 0.25%* |
| IPA | 0.75%* |
| NP-9 | 0.38%* |
| EDTA (39%) | 0.38%* |
| H₂O₂ (50%) | 0.25%* |
| Water | 97.37% |

*after dilution of 1:8 using water

SiS All Purpose Cleaner Disinfectant & Bacteria Protectant was able to eliminate 99.99% of *Klebsiella pneumoniae* (ATCC 4352), *Salmonella typhimurium* (ATCC 14028), and *Staphylococcus aureus* (ATCC 25923) inoculated.

Example 8

The utilities of Composition A-2 as an antimicrobial or biocide composition were examined.

Composition A-2 is a water-based solution of a stabilized organosilane antimicrobial agent and disinfectant that can be used to clean and disinfect poultry, agriculture and industrial facilities including food and animal processing plants. It has a number of desirable features, such as, durable, non-toxic, relatively safe, non-flammable, non-leaching and non-migrating (after it is bound), odorless, and colorless disinfectant. The formulation of Composition A-2 is shown in Table 9.

TABLE 9

| | |
|---|---|
| 3-trimethoxysilyl propyltetradecyldimethyl ammonium chloride or SiS AM7200 | 4.09% |
| N,N Diakyl ($C_{8-10}$)-N,N-dimethylammonium chloride | 1.12% |
| N-Alkyl (50% $C_{14}$, 40% $C_{12}$, 10% $C_{16}$) dimethylbenzylammonium chloride | 0.74% |
| Isopropyl alcohol | 6.00% |
| Glycol Ether EB | 6.00% |
| Barlox 12 | 2.00% |
| EDTA (39.0%) | 2.00% |
| T-NP-9.5 Surfactant | 3.00% |
| Hydrogen Peroxide (50% concentrate) | 4.00% |
| Water | 75.05% |

Composition A-2 has been proven to be effective against gram positive (e.g., *Staphylococcus aureus*) and gram negative bacteria (e.g., *E. Coli, Salmonella*, and *Pseudomonas aeruginosa*), mold and mildew (e.g., *Aspergillus niger*), yeasts (e.g., *Candida albicans*), and algae, even when diluted at ratios 1:8, 1:25, or 1:50. In addition, Composition A-2 was tested by the United States Department of Agriculture (USDA) and Department of Pathology, Faculty of Veterinary Medicine, Kasetsart University, Nakompathom, Thailand and the results demonstrated that it was effective against highly pathogenic H5N1 avian influenza virus. The USDA study indicated that a 10 minutes of incubation of a strain of Highly Pathogenic Avian Influenza virus H5N1 (HPAI virus H5N1) obtained from Indonesia with Composition A-2 (⅛-1/50 dilution) inactivated the viruses. The USDA study also demonstrated that a 5 minutes of incubation of HPAI virus H5N1 with Composition A-2 (⅛ dilution) was effective to inactivate the viruses. The Tailand study showed that Composition A-2 (⅛ dilution) was effective to inactivate a strain of HPAI virus H5N1. The Thailand study has also shown that a 1:1 (w/w) mixture of Composition A-2 with the HPAI virus H5N1 inactivated the viruses within 1 minute. In addition, the study also indicated that Composition A-2 was effective in an environment of organic matter, where most disinfectants are de-activated when exposed to organic matter (feces).

Example 9

The antimicrobial effects of cotton fabric coated with the composition of the present invention were also investigated. For example, fabric samples were immersed in a small bath containing a composition with a formulation as shown in Table 3 for about 5-10 minutes and dried at room temperature. Those fabric samples were shown to be effective at killing or reducing both vegetative cells and both gram negative and gram positive microorganisms (*Staphylococcus aureus* (ATCC 6538), *Klebsiella pneumoniae* (ATCC 4353), and *Bacillus atrophaeus* (ATCC 9372)) and killing *Bacillus* spores when challenged with those microorganisms using the standardized AATCC 100 method.

In another example, military fatigue fabrics were treated with the composition of the present invention, which conferred antimicrobial properties to the treated military fatigues fabrics. As shown in FIG. 1A and B, for instance, fatigues fabrics treated with the composition of the present invention caused a reduction in cell counts of *Klebsiella pneumoniae* and *Staphylococcus aureus* from 6-7 logs to undetectable amounts after three hours of contact.

While the foregoing invention has been described in some detail for purposes of clarity and understanding, it will be appreciated by one skilled in the art, from a reading of the disclosure, that various changes in form and detail can be made without departing from the true scope of the invention in the appended claims.

What is claimed is:

1. A method of disinfecting a substrate having a surface, comprising:
- providing a substrate having a surface;
- applying an aqueous composition having antimicrobial activity to at least a portion of the surface of the substrate, wherein the aqueous composition comprises approximately 4% by weight of an organosilane quaternary ammonium compound and approximately 2% by weight of a quaternary ammonium compound, and wherein the quaternary ammonium compound is not an organosilane quaternary ammonium compound;
- bonding at least a portion of the aqueous composition having antimicrobial activity to at least a portion of the surface of the substrate to form an antimicrobial coating on the surface of the substrate without having to modify the surface; and
- disinfecting the at least a portion of the surface of the substrate having the antimicrobial coating;
- wherein the organosilane quaternary ammonium compound is 3-trimethoxysilyl propyltetradecyldimethyl ammonium chloride; and
- wherein the quaternary ammonium compound comprises a mixture of alkyl (C14, C12 and C16) dimethyl benzyl ammonium chloride, octyl decyl dimethyl ammonium chloride, dioctyl dimethyl ammonium chloride and didecyl dimethyl ammonium chloride.

2. The method of claim 1, wherein the aqueous composition further comprises at least one agent selected from the group consisting of an oxidizing agent, a chelating agent, and a stabilizing agent.

3. The method of claim 2, wherein the aqueous composition further comprises at least one agent selected from the group consisting of hydrogen peroxide, ethylenediaminetetraacetic acid (EDTA) and a salt thereof, propylene carbonate, glycol ether, a polyol, and sucrose.

4. A method of providing an antimicrobial or disinfectant coating to a substrate having a surface, comprising:
- providing a substrate having a surface;
- applying an aqueous composition having antimicrobial activity to at least a portion of the surface of the substrate, wherein the aqueous composition comprises approximately 4% by weight of an organosilane quaternary ammonium compound and approximately 2% by weight of a quaternary ammonium compound, and wherein the quaternary ammonium compound is not an organosilane quaternary ammonium compound;
- bonding at least a portion of the aqueous composition having antimicrobial activity to at least a portion of the surface of the substrate, wherein covalently bonding at least a portion of the aqueous composition comprises covalently bonding the organosilane quaternary ammonium compound and the quaternary ammonium compound to at least a portion of the surface of the substrate without having to modify the surface; and forming an antimicrobial coating on at least a portion of the surface of the substrate, wherein the antimicrobial coating is bacteriostatic and bacteriocidal;

wherein the organosilane quaternary ammonium compound is 3-trimethoxysilyl propyltetradecyldimethyl ammonium chloride; and wherein the quaternary ammonium compound comprises a mixture of alkyl (C14, C12 and C16) dimethyl benzyl ammonium chloride, octyl decyl dimethyl ammonium chloride, dioctyl dimethyl ammonium chloride and didecyl dimethyl ammonium chloride.

5. The method of claim 4, wherein the aqueous composition further comprises at least one agent selected from the group consisting of an oxidizing agent, a chelating agent, and a stabilizing agent.

6. The method of claim 5, wherein the aqueous composition further comprises at least one agent selected from the group consisting of hydrogen peroxide, ethylenediaminetetraacetic acid (EDTA) and a salt thereof, propylene carbonate, glycol ether, a polyol, and sucrose.

7. A composition having antimicrobial activity comprising a covalently-bonded coating comprising approximately 4% by weight of an organosilane quaternary ammonium compound and approximately 2% by weight of a quaternary ammonium compound, wherein the quaternary ammonium compound is not an organosilane quaternary ammonium compound;

wherein the organosilane quaternary ammonium compound is 3-trimethoxysilyl propyltetradecyldimethyl ammonium chloride; and wherein the quaternary ammonium compound comprises a mixture of alkyl (C14, C12 and C16) dimethyl benzyl ammonium chloride, octyl decyl dimethyl ammonium chloride, dioctyl dimethyl ammonium chloride and didecyl dimethyl ammonium chloride.

8. The composition of claim 7, wherein the composition further comprises at least one agent selected from the group consisting of an oxidizing agent, a chelating agent, and a stabilizing agent.

* * * * *